United States Patent
Arai et al.

(10) Patent No.: US 11,986,147 B2
(45) Date of Patent: May 21, 2024

(54) ENDOSCOPE SYSTEM, METHOD FOR OPERATING ENDOSCOPE SYSTEM AND STORAGE MEDIUM

(71) Applicant: OLYMPUS CORPORATION, Tokyo (JP)

(72) Inventors: Risa Arai, Tama (JP); Daiki Ariyoshi, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 580 days.

(21) Appl. No.: 17/126,460

(22) Filed: Dec. 18, 2020

(65) Prior Publication Data

US 2021/0137370 A1 May 13, 2021

Related U.S. Application Data (63) Continuation of application No. PCT/JP2019/007350, filed on Feb. 26, 2019.

(30) Foreign Application Priority Data

Jun. 19, 2018 (JP) ................................ 2018-116043

(51) Int. Cl.
*A61B 1/00* (2006.01)
*A61B 1/045* (2006.01)
(Continued)

(52) U.S. Cl.
CPC ...... *A61B 1/00006* (2013.01); *A61B 1/00009* (2013.01); *A61B 1/0005* (2013.01);
(Continued)

(58) Field of Classification Search
CPC .............. A61B 1/00006; A61B 1/0655; A61B 1/00009; A61B 1/0005; A61B 1/045; A61B 1/05; A61B 1/0638; A61B 1/00; A61B 1/06; A61B 1/233; A61B 5/6844; A61B 5/6886; A61B 5/150954; A61B 1/043; A61B 1/063; A61B 1/0071
USPC ................................................. 600/103, 595
See application file for complete search history.

(56) References Cited

U.S. PATENT DOCUMENTS

2002/0014595 A1  2/2002  Sendai et al.
2004/0064016 A1*  4/2004  Kobayashi ........... A61B 5/0071
                                                         600/109
(Continued)

FOREIGN PATENT DOCUMENTS

EP    1 177 761 A2    2/2002
EP    1 609 407 A1   12/2005
(Continued)

OTHER PUBLICATIONS

International Search Report dated May 28, 2019 received in PCT/JP2019/007350.

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

An endoscope system includes a light source apparatus configured to generate first/second illumination light, an image pickup apparatus, a switching instruction device configured to be able to set one of a first observation mode in which an image obtained by image pickup of an object illuminated with the first illumination light is displayed and a second observation mode in which an image obtained by processing a color/pattern of an image obtained by image pickup of the object illuminated with the second illumination light is displayed and a processor configured to calculate a feature value indicating movement of a distal end portion of an endoscope and disable an instruction for setting the second observation mode when the feature value is equal to or higher than a predetermined threshold.

18 Claims, 5 Drawing Sheets

(51) Int. Cl.
*A61B 1/05* (2006.01)
*A61B 1/06* (2006.01)

(52) U.S. Cl.
CPC ............... *A61B 1/045* (2013.01); *A61B 1/05* (2013.01); *A61B 1/0638* (2013.01); *A61B 1/0655* (2022.02)

(56) References Cited

U.S. PATENT DOCUMENTS

| | | |
|---|---|---|
| 2009/0259098 A1 | 10/2009 | Krattiger |
| 2010/0063355 A1* | 3/2010 | Matsuura ............. A61B 1/0638 600/109 |
| 2014/0316283 A1* | 10/2014 | Kaku ................... A61B 5/0084 600/479 |
| 2015/0216460 A1* | 8/2015 | Shigeta ................ A61B 1/05 600/339 |
| 2017/0188802 A1* | 7/2017 | Lawrence ............ A61B 1/0607 |

FOREIGN PATENT DOCUMENTS

| | | |
|---|---|---|
| EP | 1 609 408 A1 | 12/2005 |
| EP | 1 609 409 A1 | 12/2005 |
| JP | 2002-045330 A | 2/2002 |
| JP | 2006-223481 A | 8/2006 |
| JP | 2007-054115 A | 3/2007 |
| JP | 2012-050641 A | 3/2012 |

\* cited by examiner

ENDOSCOPE SYSTEM, METHOD FOR OPERATING ENDOSCOPE SYSTEM AND STORAGE MEDIUM

CROSS REFERENCE TO RELATED APPLICATION

This application is a continuation application of PCT/JP2019/007350 filed on Feb. 26, 2019 and claims benefit of Japanese Application No. 2018-116043 filed in Japan on Jun. 19, 2018, the entire contents of which are incorporated herein by this reference.

BACKGROUND OF THE INVENTION

1. Field of the Invention

The present invention relates to an endoscope system, a method for operating the endoscope system and a storage medium, and more particularly, to an endoscope system, a method for operating the endoscope system and a storage medium used to observe biological tissue.

2. Description of the Related Art

In endoscopic observation in the medical field, for example, a technique that applies processing to an endoscopic image obtained by image pickup of an object including biological tissue existing inside a subject, thereby generates and displays a diagnosis supporting image including a color and/or a pattern that can identify an abnormal region included in the endoscopic image is conventionally known as a technique for supporting diagnosis of the abnormal region existing in the subject.

More specifically, Japanese Patent Application Laid-Open Publication No. 2006-223481 discloses a configuration in which by applying processing to an endoscopic image obtained by image pickup of an object irradiated with RGB frame sequential light using an electronic endoscope, a pseudo-color image corresponding to a distribution state of IHb (hemoglobin index) values in a region of interest set in the endoscopic image is generated and displayed.

SUMMARY OF THE INVENTION

An endoscope system according to one aspect of the present invention includes a light source apparatus configured to generate one of first illumination light and second illumination light as illumination light to illuminate an object, an image pickup apparatus configured to obtain an image by image pickup of the object illuminated with the illumination light, a switching instruction device configured to be able to execute an instruction for setting an observation mode for observing the object to one of a first observation mode in which a first image obtained by image pickup of the object illuminated with the first illumination light is displayed on a display apparatus and a second observation mode in which a third image obtained by processing at least one of color and pattern of a second image obtained by image pickup of the object illuminated with the second illumination light is displayed on the display apparatus and a processor. The processor calculates a feature value indicating movement of a distal end portion of an endoscope provided with the image pickup apparatus based on the first image or the second image, determines whether the feature value indicating the movement of the distal end portion of the endoscope immediately before the observation mode is switched from the first observation mode to the second observation mode is equal to or higher than a predetermined threshold, and disables the instruction for setting the observation mode to the second observation mode executed by the switching instruction device when the processor determines that the feature value is equal to or higher than the predetermined threshold.

A method for operating an endoscope system according to one aspect of the present invention includes generating one of first illumination light and second illumination light as illumination light to illuminate an object, obtaining an image by image pickup of the object illuminated with the illumination light, executing an instruction for setting an observation mode for observing the object to one of a first observation mode in which a first image obtained by image pickup of the object illuminated with the first illumination light is displayed on a display apparatus and a second observation mode in which a third image obtained by processing at least one of a color and a pattern of a second image obtained by image pickup of the object illuminated with the second illumination light is displayed on the display apparatus, calculating a feature value indicating movement of a distal end portion of an endoscope based on the first image or the second image, determining whether the feature value indicating the movement of the distal end portion of the endoscope immediately before the observation mode is switched from the first observation mode to the second observation mode is equal to or higher than a predetermined threshold, and disabling the instruction for setting the observation mode to the second observation mode when it is determined that the feature value is equal to or higher than the predetermined threshold.

A storage medium according to one aspect of the present invention is a non-transitory computer-readable storage medium that stores a computer program, the computer program causing a computer to perform control including generating one of first illumination light and second illumination light as illumination light to illuminate an object, obtaining an image by image pickup of the object illuminated with the illumination light, executing an instruction for setting an observation mode for observing the object to one of a first observation mode in which a first image obtained by image pickup of the object illuminated with the first illumination light is displayed on a display apparatus and a second observation mode in which a third image obtained by processing at least one of a color and a pattern of a second image obtained by image pickup of the object illuminated with the second illumination light is displayed on the display apparatus, calculating a feature value indicating movement of a distal end portion of an endoscope based on the first image or the second image, determining whether the feature value indicating the movement of the distal end portion of the endoscope immediately before the observation mode is switched from the first observation mode to the second observation mode is equal to or higher than a predetermined threshold, and disabling the instruction for setting the observation mode to the second observation mode when it is determined that the feature value is equal to or higher than the predetermined threshold.

DETAILED DESCRIPTION OF THE PREFERRED EMBODIMENT

Hereinafter, an embodiment of the present invention will be described with reference to the accompanying drawings.

FIG. 1 to FIG. 7 relate to an embodiment of the present invention.

Figure 1:
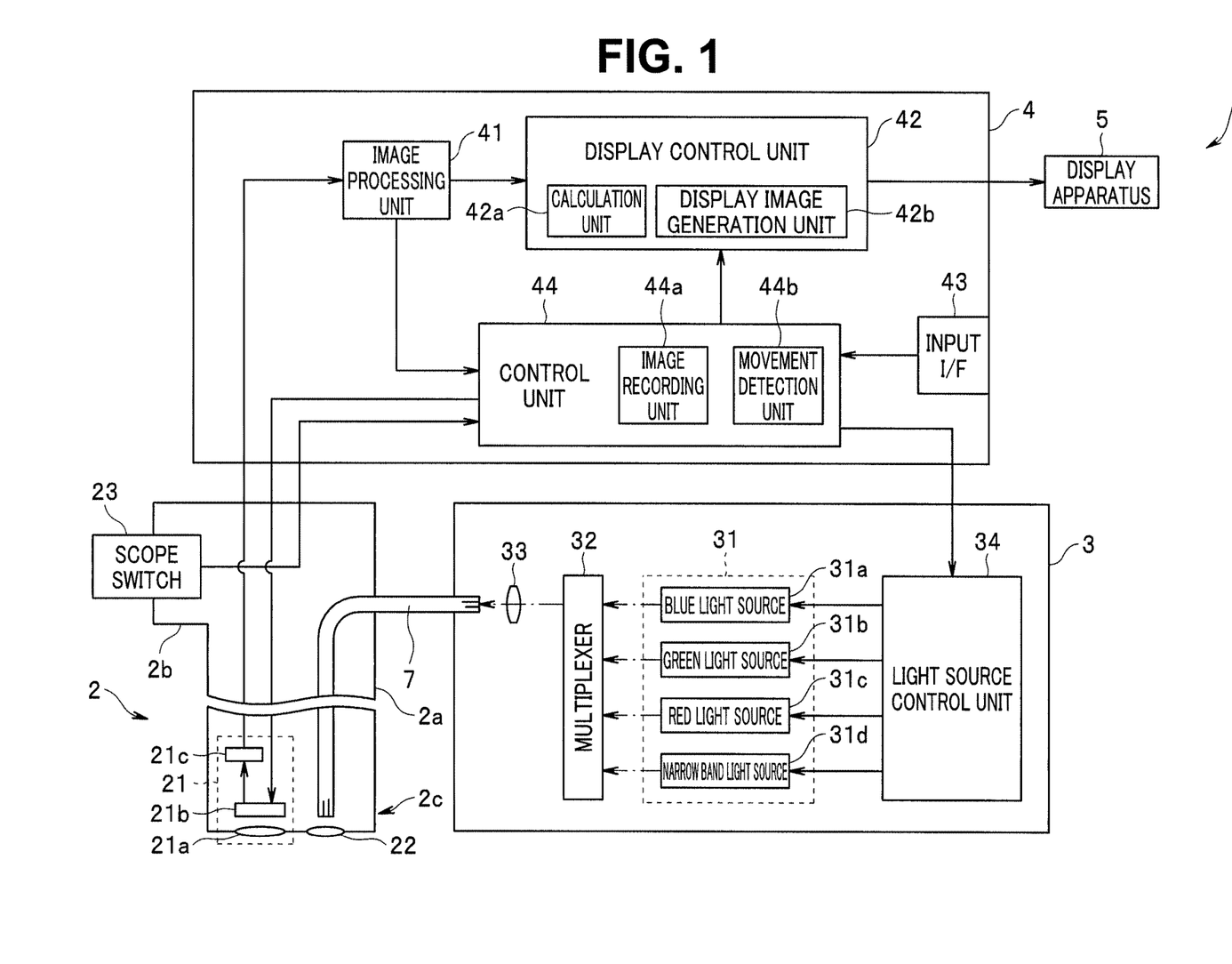
FIG. 1 is a diagram illustrating a configuration of main parts of an endoscope system according to an embodiment.

As shown in FIG. 1, an endoscope system 1 includes an endoscope 2 insertable into a subject and configured to output an endoscopic image obtained by image pickup of an object such as biological tissue existing inside the subject, a light source apparatus 3 configured to supply illumination light used to observe the object via a light guide 7 inserted and disposed inside the endoscope 2, a processor 4 configured to perform operation to output a display image in accordance with an endoscopic image outputted from the endoscope 2 and a display apparatus 5 configured to display a display image or the like outputted from the processor 4. FIG. 1 is a diagram illustrating a configuration of main parts of the endoscope system according to the embodiment.

The endoscope 2 includes an insertion portion 2a formed into an elongated shape insertable into the subject and an operation portion 2b provided on a proximal end side of the insertion portion 2a. The endoscope 2 is detachably connected to the processor 4 via a universal cable (not shown) incorporating a signal line to be used to transmit an endoscopic image or the like outputted from, for example, an image pickup unit 21 (which will be described later). Furthermore, the endoscope 2 is detachably connected to the light source apparatus 3 via a light guide cable (not shown) in which at least part of the light guide 7 is incorporated.

The image pickup unit 21 configured to pick up an image of an object such as biological tissue inside the subject, an emission end portion of the light guide 7 and an illumination optical system 22 configured to radiate illumination light transmitted from the light guide 7 to the object are provided at a distal end portion 2c of the insertion portion 2a.

The image pickup unit 21 is an image pickup apparatus configured to pick up an image of an object illuminated with illumination light that has passed through the illumination optical system 22 to generate an endoscopic image, and output the generated endoscopic image to the processor 4. In other words, the image pickup unit 21 is configured to obtain an endoscopic image by image pickup of the object illuminated with illumination light that has passed through the illumination optical system 22 and obtain an endoscopic image. The image pickup unit 21 is constructed of an objective optical system 21a, an image pickup device 21b, and an analog front end (hereinafter, abbreviated as "AFE") 21c.

The objective optical system 21a includes, for example, an optical element such as a lens and is configured to form an image of return light (reflected light) emitted from the object illuminated with the illumination light that has passed through the illumination optical system 22.

The image pickup device 21b is constructed of an image sensor such as a CCD or a CMOS. A primary color Bayer array color filter configured to spectrally divide return light incident from the objective optical system 21a into three colors: red, green and blue, and a plurality of pixels disposed in matrix form configured to pick up an image of light that has passed through the color filter are provided on the image pickup surface of the image pickup device 21b. The image pickup device 21b is configured to generate an image pickup signal by picking up an image of the return light formed by the objective optical system 21a and output the generated image pickup signal to an AFE 21c. The image pickup device 21b is also configured to perform operation according to a control signal outputted from the processor 4.

The AFE 21c is configured to apply predetermined signal processing such as noise reduction processing and A/D conversion processing to the image pickup signal outputted from the image pickup device 21b to thereby generate an endoscopic image (endoscopic image data) and output the generated endoscopic image to the processor 4.

The operation portion 2b is configured to have a shape that allows the user to grasp for operation. The operation portion 2b is provided with a scope switch 23 including one or more switches that can execute instructions according to the user's input operation to the processor 4. More specifically, the scope switch 23 is provided with an observation mode switchover switch (not shown) that can set (switch) the observation mode of the endoscope system 1 to one of a normal observation mode and a diagnosis support mode depending on, for example, the user's operation. The scope switch 23 is also provided with a release switch (not shown) that can execute a release instruction for recording an endoscopic image obtained by image pickup of the object by the endoscope 2 as a still image depending on, for example, the user's operation.

In other words, the scope switch 23 is a switching instruction device provided with a function as a switching instruction unit and configured to be able to execute an instruction for setting the observation mode (of the endoscope system 1) when observing an image of the object picked up by the endoscope 2 to at least one of a normal observation mode in which an endoscopic image WDI (which will be described later) is displayed on the display apparatus 5 and a diagnosis support mode in which a diagnosis support image SDS (which will be described later) obtained by processing at least one of a color and a pattern of the endoscopic image SDI (which will be described later) is displayed on the display apparatus 5.

The light source apparatus 3 has a function as a light source unit and is configured to generate one of illumination light WL and illumination light SL (both will be described later) as illumination light to illuminate the object existing inside the subject. The light source apparatus 3 is constructed of a light emission unit 31, a multiplexer 32, a condensing lens 33 and a light source control unit 34.

The light emission unit 31 is constructed of a blue light source 31a, a green light source 31b, a red light source 31c and a narrow band light source 31d.

Figure 2:
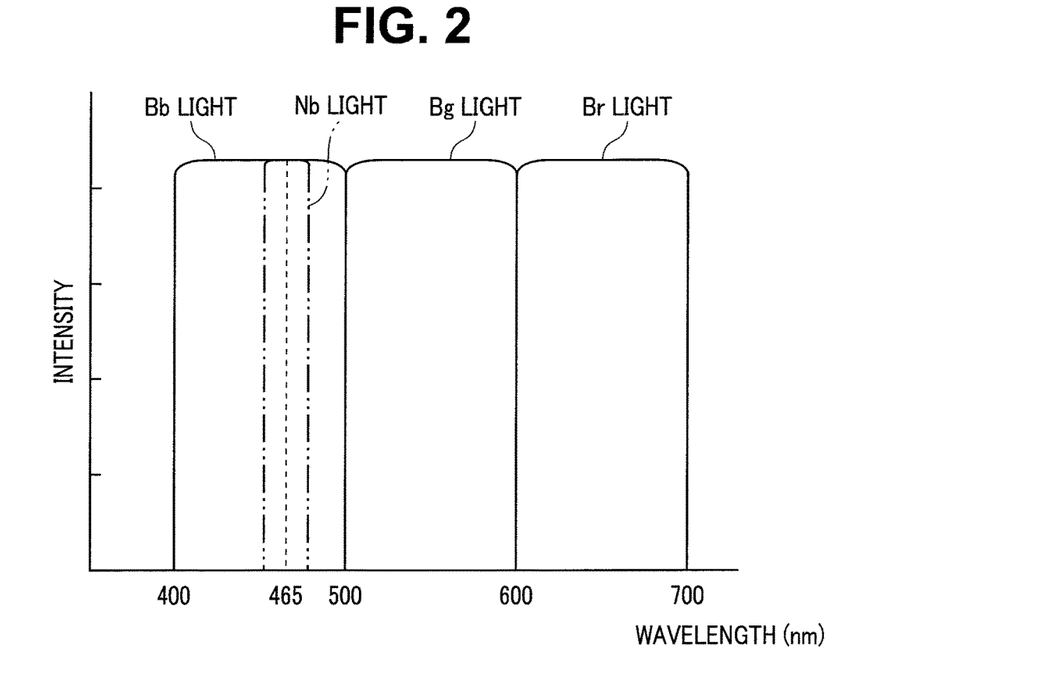
FIG. 2 is a diagram illustrating wavelength band examples of light emitted from a light source apparatus of the endoscope system according to the embodiment.

The blue light source 31a includes, for example, a light-emitting device such as a blue LED. The blue light source 31a is configured to generate blue light having intensity in a blue color gamut (hereinafter, called "Bb light"). More specifically, the blue light source 31a is configured to generate light having intensity in a wavelength band of 400 nm to 500 nm as Bb light as shown in FIG. 2. The blue light source 31a is also configured to emit light or extinguish light in accordance with a light source drive signal supplied from the light source control unit 34. The blue light source 31a is configured to emit light with a light emission quantity corresponding to the light source drive signal supplied from the light source control unit 34. FIG. 2 is a diagram illustrating wavelength band examples of light emitted from the light source apparatus of the endoscope system according to the embodiment.

The green light source 31b includes, for example, a light-emitting device such as a green LED. The green light source 31b is configured to generate green light having intensity in a green color gamut (hereinafter, called "Bg light"). More specifically, the green light source 31b is configured to generate light having intensity in a wavelength band of 500 nm to 600 nm as Bg light as shown in FIG. 2. The green light source 31b is also configured to emit light or extinguish light in accordance with a light source drive signal supplied from the light source control unit 34. The green light source 31b is configured to emit light with a light emission quantity corresponding to the light source drive signal supplied from the light source control unit 34.

The red light source 31c includes, for example, a light-emitting device such as a red LED. The red light source 31c is configured to generate red light having intensity in a red color gamut (hereinafter, called "Br light"). More specifically, the red light source 31c is configured to generate light having intensity in a wavelength band of 600 nm to 700 nm as Br light as shown in FIG. 2. The red light source 31c is also configured to emit light or extinguish light in accordance with a light source drive signal supplied from the light source control unit 34. The red light source 31c is configured to emit light with a light emission quantity corresponding to the light source drive signal supplied from the light source control unit 34.

Figure 3:
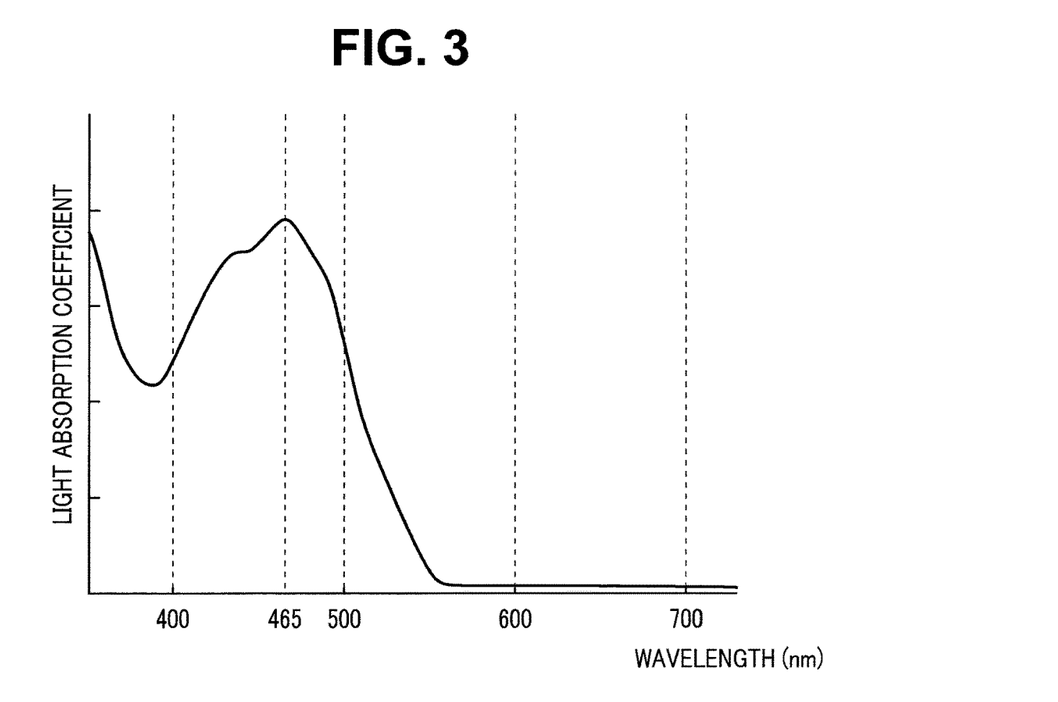
FIG. 3 is a diagram illustrating an example of a light absorption characteristic of plasma.

The narrow band light source 31d includes, for example, a light-emitting device such as a blue LED. The narrow band light source 31d is configured to generate narrow band light having intensity in a blue color gamut and a wavelength band narrower than Bb light (hereinafter, called "Nb light"). More specifically, the narrow band light source 31d is configured to generate light having a wavelength band narrower than Bb light, a central wavelength of which is set in the vicinity of 465 nm as Nb light. In other words, the central wavelength of Nb light is set as a wavelength that matches or substantially matches a peak wavelength in a plasma light absorption characteristic illustrated in FIG. 3. The narrow band light source 31d is also configured to emit light or extinguish light in accordance with a light source drive signal supplied from the light source control unit 34. The narrow band light source 31d is configured to emit light with a light emission quantity corresponding to the light source drive signal supplied from the light source control unit 34. FIG. 3 is a diagram illustrating an example of a light absorption characteristic of plasma.

Note that in the present embodiment, the central wavelength of Nb light needs only to be set to any one wavelength belonging to a range from 415 nm to 495 nm.

The multiplexer 32 is configured to be able to multiplex light emitted from the light emission unit 31 and make the multiplexed light incident onto the condensing lens 33.

The condensing lens 33 is configured to condense light made incident through the multiplexer 32 and emit the condensed light to an incident end portion of the light guide 7.

The light source control unit 34 includes, for example, a control circuit and a drive circuit. The light source control unit 34 is configured to generate and output a light source drive signal to drive each light source of the light emission unit 31 in accordance with a control signal outputted from the processor 4.

The processor 4 includes an image processing unit 41, a display control unit 42, an input I/F (interface) 43 and a control unit 44.

The image processing unit 41 includes, for example, an image processing circuit. The image processing unit 41 is configured to apply image processing such as white balance adjustment and gamma correction to the endoscopic image outputted from the endoscope 2 and output the endoscopic image subjected to the image processing to the display control unit 42 and the control unit 44.

The display control unit 42 includes, for example, a display control circuit. The display control unit 42 is configured to perform operation to output a display image corresponding to a control signal outputted from the control unit 44 to the display apparatus 5. The display control unit 42 includes a calculation unit 42a and a display image generation unit 42b.

The calculation unit 42a is configured to perform calculation processing using an endoscopic image outputted through the image processing unit 41. Note that a specific example of the processing carried out by the calculation unit 42a will be described later.

The display image generation unit 42b is configured to perform processing to generate a diagnosis support image including visual information based on which an abnormal region included in the endoscopic image can be identified, by processing at least one of a color and a pattern of the endoscopic image outputted through the image processing unit 41 based on the processing result obtained through calculation processing by the calculation unit 42a. Note that a specific example of the processing carried out by the display image generation unit 42b will be described later.

The input I/F 43 is provided with one or more switches that can execute an instruction corresponding to the user's input operation on the control unit 44. More specifically, the input I/F 43 is provided with an observation mode switchover switch (not shown) configured to be able to set (switch) the observation mode of the endoscope system 1 to one of the normal observation mode and the diagnosis support mode depending on the user's operation. The input I/F 43 is also provided with a release switch (not shown) configured to be able to execute a release instruction for recording the endoscopic image obtained by image pickup of the object by the endoscope 2 as a still image depending on the user's operation.

In other words, the input I/F 43 is a switching instruction device provided with a function as a switching instruction unit and is configured to be able to execute an instruction for setting the observation mode (of the endoscope system 1) when observing an image of the object picked up by the endoscope 2 to one of the normal observation mode in which the endoscopic image WDI is displayed on the display apparatus 5 and the diagnosis support mode in which a diagnosis support image SDS obtained by processing at least one of a color and a pattern of the endoscopic image SDI is displayed on the display apparatus 5.

The control unit 44 includes, for example, a control circuit. The control unit 44 is configured to perform operation in accordance with an instruction executed by the scope switch 23 or the input I/F 43. The control unit 44 is configured to generate and output a control signal to control the operation of the image pickup device 21b. The control unit 44 is configured to generate and output a control signal to control the operation of each light source of the light emission unit 31 via the light source control unit 34. The control unit 44 includes an image recording unit 44a and a movement detection unit 44b.

The image recording unit 44a is configured to perform operation to record an endoscopic image outputted through the image processing unit 41 as a movement detection image. When a release instruction is executed, the image recording unit 44a is configured to perform operation to record an endoscopic image outputted through the image processing unit 41 as a release image (still image).

The movement detection unit 44b is configured to perform movement detection processing to calculate a feature value indicating movement of the distal end portion 2c based on the movement detection image recorded in the image recording unit 44a. Note that a specific example of processing carried out by the movement detection unit 44b will be described later.

Note that in the present embodiment, the respective components of the processor 4 may be configured as individual electronic circuits or may be configured as circuit blocks in an integrated circuit such as an FPGA (field programmable gate array). In the present embodiment, for example, the processor 4 may include one or more CPUs. The configuration according to the present embodiment may be modified as appropriate so that a computer (not shown) reads a computer program to execute the functions of the respective components of the processor 4 from a storage medium such as a memory and operates according to the read computer program.

The display apparatus 5 is provided with, for example, an LCD (liquid crystal display) and configured to be able to display a display image or the like outputted from the processor 4.

Figure 4:
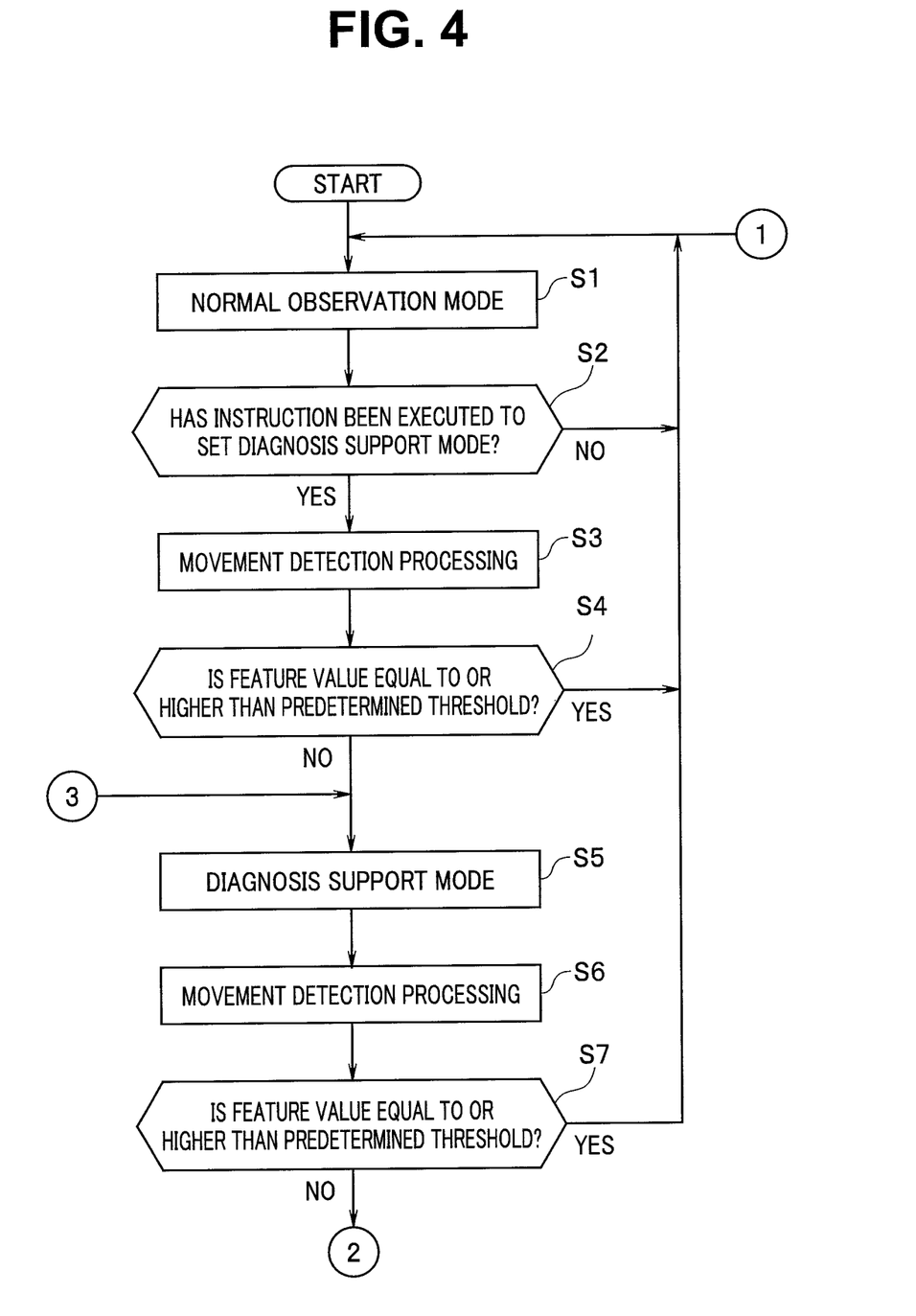
FIG. 4 is a flowchart illustrating part of a specific example of processing or the like carried out in the endoscope system according to the embodiment.
Figure 5:
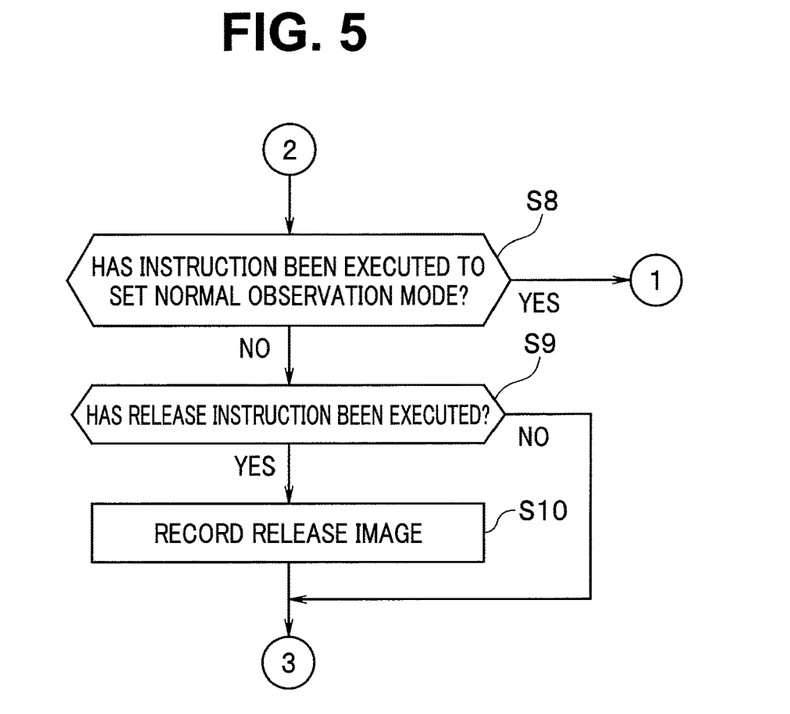
FIG. 5 is a flowchart illustrating a continuation of the processing in FIG. 4.

Next, operation of the present embodiment will be described with reference to FIG. 4 and FIG. 5 or the like. Note that a case will be described hereinafter as an example where the insertion portion 2a is inserted into a nasal cavity of an examinee and the image pickup unit 21 picks up an image of the object including biological tissue (mucous membrane or the like) existing in the nasal cavity of the examinee. FIG. 4 is a flowchart illustrating part of a specific example of processing or the like carried out in the endoscope system according to the embodiment. FIG. 5 is a flowchart illustrating a continuation of the processing in FIG. 4. The processing shown in FIG. 4 and FIG. 5 may also be implemented by the computer reading a computer program stored in the storage medium and executing the program.

The user such as an operator connects the respective components of the endoscope system 1, turns on power, then operates the observation mode switchover switch of the scope switch 23 or input I/F 43 to execute an instruction for setting the observation mode of the endoscope system 1 to the normal observation mode.

When detecting that the instruction for setting the observation mode of the endoscope system 1 to the normal observation mode has been executed, the control unit 44 generates and outputs a control signal to operate in accordance with the normal observation mode (step S1 in FIG. 4). In accordance with a processing result or the like obtained by processing which will be described later, the control unit 44 performs operation to maintain the observation mode of the endoscope system 1 in the normal observation mode or operation to switch the observation mode of the endoscope system 1 from the diagnosis support mode to the normal observation mode (step S1 in FIG. 4).

In step S1 in FIG. 4, the control unit 44 generates control signals to emit Bb light, Bg light and Br light from the light source apparatus 3 and outputs the control signals to the light source control unit 34. In step S1 in FIG. 4, the control unit 44 generates a control signal to cause the display apparatus 5 to display an endoscopic image WDI (which will be described later) outputted through the image processing unit 41 and outputs the control signal to the display control unit 42. In step S1 in FIG. 4, the control unit 44 causes the image recording unit 44a to record endoscopic images WDI corresponding to a predetermined time period PA outputted through the image processing unit 41 as movement detection images MDI. Note that the predetermined time period PA may be set as a time period according to the size or the like of the nasal cavity of the examinee.

According to the control signal outputted from the control unit 44, the light source control unit 34 generates and outputs a light source drive signal to extinguish light of the narrow band light source 31d and cause the blue light source 31a, the green light source 31b and the red light source 31c to simultaneously emit light in the normal observation mode. In accordance with such an operation of the light source control unit 34, illumination light WL including Bb light, Bg light and Br light in the normal observation mode is emitted from the light source apparatus 3 (light emission unit 31), the object is irradiated with the illumination light WL and the endoscopic image WDI obtained by picking up an image of return light (reflected light) of the illumination light WL is outputted from the image pickup unit 21 to the image processing unit 41.

The image processing unit 41 applies image processing such as white balance adjustment and gamma correction to the endoscopic image WDI outputted from the endoscope 2 and outputs the endoscopic image WDI subjected to the image processing to the display control unit 42 and the control unit 44.

In accordance with the control signal outputted from the control unit 44, the display control unit 42 performs operation to output the endoscopic image WDI outputted through the image processing unit 41 to the display apparatus 5 as a display image in the normal observation mode.

In the normal observation mode, the image recording unit 44a performs operation to sequentially record the endoscopic images WDI corresponding to a predetermined time period PA outputted through the image processing unit 41 as movement detection images MDI. Note that it is assumed that time point information based on which a time point such as a time stamp recorded by the image recording unit 44a can be identified is added to each of the movement detection image MDI recorded in the image recording unit 44a.

The user inserts the insertion portion 2a of the endoscope 2 into the nasal cavity of the examinee while watching the endoscopic image WDI displayed on the display apparatus 5 and disposes the distal end portion 2c in the vicinity of a desired object existing inside the nasal cavity of the examinee. After that, with the distal end portion 2c of the endoscope 2 disposed in the vicinity of the desired object, the user operates the observation mode switchover switch of the scope switch 23 or the input I/F 43 to thereby execute an instruction for setting the observation mode of the endoscope system 1 to the diagnosis support mode.

The control unit 44 performs determination processing on whether an instruction for setting the observation mode of the endoscope system 1 to the diagnosis support mode has been executed or not (step S2 in FIG. 4).

When the control unit 44 has not successfully detected the instruction for setting the observation mode of the endoscope system 1 to the diagnosis support mode (S2: NO), the control unit 44 performs the operation in step S1 in FIG. 4. In other words, when the operation in step S1 is performed after step S2 in FIG. 4, the observation mode of the endoscope system 1 is maintained in the normal observation mode and, as the display image displayed on the display apparatus 5, the endoscopic image WDI is maintained.

When the control unit 44 has successfully detected the instruction for setting the observation mode of the endoscope system 1 to the diagnosis support mode (S2: YES), the control unit 44 causes the image recording unit 44a to record the endoscopic images WDI corresponding to a predetermined time period PB outputted through the image processing unit 41 as a movement detection image MDI. Note that the predetermined time period PB may be set as a time period depending on the size or the like of the nasal cavity of the examinee.

The image recording unit 44a performs operation to sequentially record the endoscopic images WDI outputted from the image processing unit 41 as the movement detection images MDI for a predetermined time period PB using timing at which the instruction for setting the observation mode of the endoscope system 1 to the diagnosis support mode is detected (by the control unit 44) as a starting point.

In other words, according to the present embodiment, the endoscopic images WDI outputted from the image processing unit 41 are sequentially recorded in the image recording unit 44a as the movement detection images MDI for each of the predetermined time period PA before the instruction for setting the observation mode of the endoscope system 1 to the diagnosis support mode is executed and the predetermined time period PB corresponding to the time period continuous to the predetermined time period PA after the instruction is executed.

The movement detection unit 44b performs movement detection processing to calculate a feature value FVA indicating movement of the distal end portion 2c immediately before the observation mode of the endoscope system 1 is switched from the normal observation mode to the diagnosis support mode based on the movement detection image MDI recorded in the image recording unit 44a (step S3 in FIG. 4). In other words, the movement detection unit 44b detects the movement of the distal end portion 2c of the endoscope 2 provided with the image pickup unit 21 based on the endoscopic image WDI recorded in the image recording unit 44a. Furthermore, the movement detection unit 44b acquires the feature value FVA as the detection result of the movement of the distal end portion 2c.

Here, a specific example of the processing carried out by the movement detection unit 44b will be described hereinafter.

The movement detection unit 44b extracts, for example, two movement detection images: a movement detection image MDIA and a movement detection image MDIB recorded after the movement detection image MDIA from among the plurality of movement detection images MDI recorded in the image recording unit 44a. The movement detection unit 44b calculates a time interval TNA corresponding to a time lag generated when the two movement detection images MDIA and MDIB are recorded based on time point information added to the two movement detection images MDIA and MDIB respectively. The movement detection unit 44b calculates the feature value FVA through calculations by applying the time interval TNA, the calculated value CVA calculated based on a pixel value of the movement detection image MDIA and the calculated value CVB calculated based on the pixel value of the movement detection image MDIB to Equation (1) below.

$$FVA=(CVB-CVA)/TNA \quad (1)$$

According to the present embodiment, the calculated values CVA and CVB may be calculated using any one of calculation methods listed below as long as the calculated values CVA and CVB are calculated using a common calculation method. Note that the calculated values CVA and CVB will be generically described as a calculated value CVX and movement detection images used to calculate the calculated value CVX will be generically described as MDIX hereinafter for simplicity of description.

The calculated value CVX may also be calculated as average values of blue pixel value Vbm, green pixel value Vgm and red pixel value Vrm for all pixels included in a predetermined calculation region CRA set, for example, in the movement detection image MDIX.

The calculated value CVX may also be calculated by calculating (Vrm+Vgm)/Vbm (calculation for normalizing the sum of the pixel value Vrm and the pixel value Vgm by the pixel value Vbm) for the respective pixels included in the predetermined calculation region CRA set, for example, in the movement detection image MDIX and as an average value of the respective values obtained through the calculation.

The calculated value CVX may also be calculated, for example, as an average value of a blue pixel value Vbm in all pixels included in the predetermined calculation region CRA set in the movement detection image MDIX.

The calculated value CVX may also be calculated as an average value of a red pixel value Vrm for all pixels included in the predetermined calculation region CRA set, for example, in the movement detection image MDIX.

The calculated value CVX may also be calculated, for example, as an average value of a green pixel value Vgm for all pixels included in the predetermined calculation region CRA set in the movement detection image MDIX.

Figure 6:
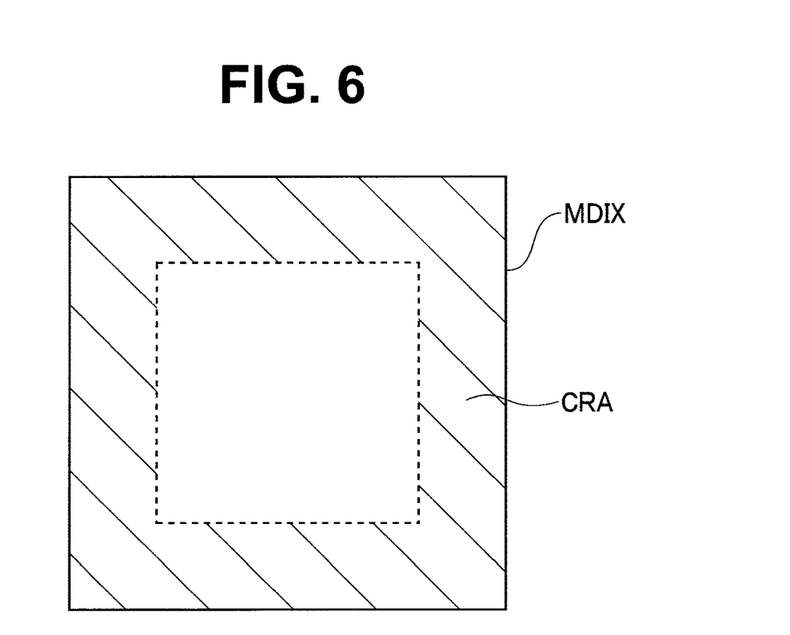
FIG. 6 is a diagram illustrating a specific example of a calculation region set in a movement detection image.
Figure 7:
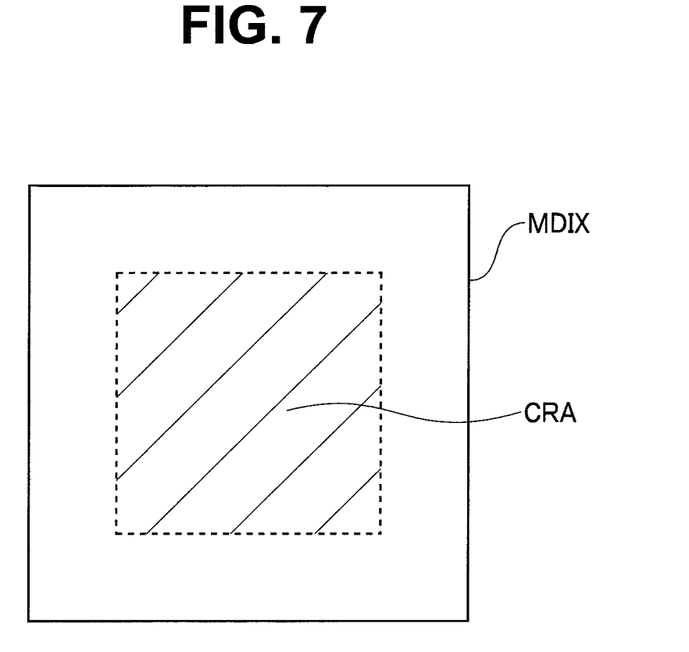
FIG. 7 is a diagram illustrating a specific example of the calculation region set in the movement detection image.

The predetermined calculation region CRA may also be set as a whole region of the movement detection image MDIX or may be set as a region of part of the movement detection image MDIX. More specifically, the predetermined calculation region CRA may also be a rectangle frame-shaped region set according to, for example, a distance from the end portion of the movement detection image MDIX (see FIG. 6) or may be a rectangular region set according to a distance from the center of the movement detection image MDIX (see FIG. 7). FIG. 6 and FIG. 7 are diagrams illustrating specific examples of the calculation region set in the movement detection image.

In other words, as the processing to detect movement of the distal end portion 2c, the movement detection unit 44b performs processing of calculating a feature value based on the pixel value of each pixel included in the predetermined calculation region CRA set according to the distance from the center of the movement detection image MDT. As the processing to detect movement of the distal end portion 2c, the movement detection unit 44b performs processing of calculating a feature value based on the pixel value of each pixel included in the predetermined calculation region CRA set according to the distance from the end portion of the movement detection image MDI.

The control unit 44 performs determination processing on whether the feature value FVA indicating movement of the distal end portion 2c calculated by the movement detection unit 44b is equal to or higher than a predetermined threshold THA (step S4 in FIG. 4).

After obtaining a judgement result that the feature value FVA calculated by the movement detection unit 44b is equal to or higher than the threshold THA (S4: YES), the control unit 44 performs the operation in step S1 in FIG. 4. In other words, when it is determined based on the detection result of the movement detection unit 44b that the feature value FVA indicating the movement of the distal end portion 2c immediately before the observation mode of the endoscope system 1 is switched from the normal observation mode to the diagnosis support mode is equal to or higher than the predetermined threshold THA, the control unit 44 disables the instruction for setting the observation mode set in the scope switch 23 or the input I/F 43 to the diagnosis support mode. When the operation in step S1 is performed after step S2 to step S4, the observation mode of the endoscope system 1 is maintained in the normal observation mode as the instruction detected in step S2 in FIG. 4 is disabled, and as the display image displayed on the display apparatus 5, the endoscopic image WDI is maintained.

After obtaining a judgement result that the feature value FVA calculated by the movement detection unit 44b is less than the threshold THA (S4: NO), the control unit 44 generates and outputs a control signal to perform operation corresponding to the diagnosis support mode (step S5 in FIG. 4). The control unit 44 performs operation to maintain the observation mode of the endoscope system 1 in the diagnosis support mode according to a processing result obtained by processing, which will be described later (step S5 in FIG. 4).

In step S5 in FIG. 4, the control unit 44 generates control signals to emit Nb light, Bg light and Br light from the light source apparatus 3 and outputs the control signals to the light source control unit 34. In step S5 in FIG. 4, the control unit 44 causes the image recording unit 44a to record the endoscopic image SDI corresponding to a predetermined time period PC outputted through the image processing unit 41 (which will be described later) as the movement detection image MDI. Note that the predetermined time period PC may be set as a time period corresponding to, for example, the size or the like of the nasal cavity of the examinee. In step S5 in FIG. 4, the control unit 44 generates a control signal to display the diagnosis support image SDS corresponding to the endoscopic image SDI outputted through the image processing unit 41 on the display apparatus 5 and outputs the control signal to the display control unit 42.

The light source control unit 34 generates and outputs a light source drive signal to cause the green light source 31b, the red light source 31c and the narrow band light source 31d to simultaneously emit light while causing the blue light source 31a to extinguish light in the diagnosis support mode in response to the control signal outputted from the control unit 44. Depending on such an operation of the light source control unit 34, illumination light SL including Nb light, Bg light and Br light is emitted from the light source apparatus 3 (light emission unit 31) in the diagnosis support mode, the object is irradiated with the illumination light SL and an endoscopic image SDI obtained by picking up an image of return light (reflected light) of the illumination light SL is outputted from the image pickup unit 21 to the image processing unit 41.

The image processing unit 41 applies image processing such as white balance adjustment and gamma correction to the endoscopic image SDI outputted from the endoscope 2 and outputs the endoscopic image SDI subjected to the image processing to the display control unit 42 and the control unit 44 respectively.

In response to the control signal outputted from the control unit 44, the display control unit 42 generates a diagnosis support image SDS in response to the endoscopic image SDI outputted through the image processing unit 41 in the diagnosis support mode and performs operation to output the generated diagnosis support image SDS to the display apparatus 5 as a display image.

Here, a specific example of the method for generating a diagnosis support image SDS displayed on the display apparatus 5 in the diagnosis support mode will be described.

The calculation unit 42a performs calculation processing to calculate an index value IVA indicating a degree of abnormality of biological tissue included in the endoscopic image SDI for each pixel of the endoscopic image SDI outputted through the image processing unit 41. The calculation unit 42a then acquires the calculation result of the index value IVA for each pixel of the endoscopic image SDI as a processing result of the calculation processing.

Note that the index value IVA may be calculated through calculations using any one index calculation expression of (Vrn+Vgn)/Vbn, Vrn/Vgn, Vrn/Vbn and Vgn/Vbn, where, for example, a blue pixel value is Vbn, a green pixel value is Vgn and a red pixel value is Vrn for each pixel included in the endoscopic image SDI. Alternatively, the index value IVA may also be calculated through calculations using expressions obtained by reversing the denominator and the numerator of any one calculation expression of (Vrn+Vgn)/Vbn, Vrn/Vgn, Vrn/Vbn and Vgn/Vbn. In other words, the index value IVA may be calculated as any one of a value obtained by normalizing the sum of Vrn and Vgn by Vbn, a value obtained by normalizing Vrn by Vgn, a value obtained by normalizing Vrn by Vbn and a value obtained by normalizing Vgn by Vbn.

The display image generation unit 42b processes at least one of a color and a pattern of the endoscopic image SDI outputted through the image processing unit 41 based on the processing result obtained through calculation processing by the calculation unit 42a to thereby generate a diagnosis support image SDS including visual information based on which an abnormal region included in the endoscopic image can be identified.

More specifically, the display image generation unit 42b performs processing so as to classify the index value IVA calculated for each pixel of the endoscopic image SDI into any one of a plurality of numerical value ranges based on the processing result obtained by the calculation processing by the calculation unit 42a and replace the pixel information included in each pixel with pixel information corresponding to the color and/or pattern corresponding to the classified numerical value range to thereby generate a diagnosis support image SDS. According to such processing, a diagnosis support image SDS with different colors and/or patterns assigned to a normal region included in the endoscopic image SDI and an abnormal region included in the endoscopic image SDI is generated.

The image recording unit 44a performs operation to sequentially record the endoscopic images SDI corresponding to a predetermined time period PC outputted through the image processing unit 41 as movement detection images MDI in the diagnosis support mode.

The movement detection unit 44b performs movement detection processing to calculate a feature value FVB indicating the movement of the distal end portion 2c when the observation mode of the endoscope system 1 is set to the diagnosis support mode based on the movement detection image MDI recorded in the image recording unit 44a (step S6 in FIG. 4). In other words, the movement detection unit 44*b* detects the movement of the distal end portion 2*c* of the endoscope 2 provided with the image pickup unit 21 based on the endoscopic image SDI recorded in the image recording unit 44*a*. Furthermore, the movement detection unit 44*b* acquires a feature value FVB as a detection result of the movement of the distal end portion 2*c*.

More specifically, the movement detection unit 44*b* calculates calculated values CVA and CVB using one of the calculation methods of the aforementioned index value IVA and calculates the feature value FVB through calculations by applying the calculated values CVA and CVB which are calculated and the time interval TNA calculated using the aforementioned calculation method to Expression (1) above.

The control unit 44 performs determination processing on whether the feature value FVB indicating the movement of the distal end portion 2*c* calculated by the movement detection unit 44*b* is equal to or higher than a predetermined threshold THB or not (step S7 in FIG. 4).

After obtaining a judgement result that the feature value FVB calculated by the movement detection unit 44*b* is less than a threshold THB (S7: NO), the control unit 44 performs operation in step S8 in FIG. 5, which will be described later.

After obtaining a judgement result that the feature value FVB calculated by the movement detection unit 44*b* is equal to or higher than the threshold THB (S7: YES), the control unit 44 performs the operation in step S1 in FIG. 4. In other words, when the control unit 44 determines that the feature value FVB indicating the movement of the distal end portion 2*c* in the diagnosis support mode based on the detection result of the movement detection unit 44*b* is equal to or higher than the predetermined threshold THB, the control unit 44 performs control to set the observation mode of the endoscope system 1 to the normal observation mode. When the operation in step S1 is performed after step S5 to step S7, the observation mode of the endoscope system 1 is switched from the diagnosis support mode to the normal observation mode according to the movement of the distal end portion 2*c* in the diagnosis support mode and the display image displayed on the display apparatus 5 is switched from the diagnosis support image SDS to the endoscopic image WDI.

Note that the threshold THB may be set as a single value that can be used in each region inside the nasal cavity or may be set as a plurality of values that can be used differently depending on the plurality of regions in the nasal cavity. More specifically, as the threshold THB that can be used in the processing in step S7 in FIG. 4, a paranasal sinus threshold THB1 and a middle nasal meatus threshold THB2 set to a value smaller than the threshold THB1 may be set respectively. In such a case, for example, a switch or the like that can execute an instruction for selecting any one threshold THB to be used in the processing in step S7 in FIG. 4 from the thresholds THB1 and THB2 may be provided in the scope switch 23 or the input I/F 43.

According to the present embodiment, when the control unit 44 determines in step S7 in FIG. 4 that the feature value indicating the movement of the distal end portion 2*c* is equal to or higher than a predetermined threshold based on the detection result of the movement detection unit 44*b*, the control unit 44 may perform operation to generate a control signal to cause the display apparatus 5 to display visual information such as a character string that can notify a state relating to the movement of the distal end portion 2*c* of the endoscope 2 together with the diagnosis support image SDS and output the visual information to the display control unit 42. According to such an operation, in the diagnosis support mode, it is possible to cause the display apparatus 5 to display the display image in which an alert message indicating that the distal end portion 2*c* is approaching a wall surface (mucous membrane) in the nasal cavity is superimposed on the diagnosis support image SDS. According to the present embodiment, a voice corresponding to the aforementioned alert message may be generated from a speaker (not shown) or the like.

According to the present embodiment, for example, when the control unit 44 detects that a predetermined time period has elapsed after setting the observation mode of the endoscope system 1 to the diagnosis support mode in response to an instruction executed by the scope switch 23 or the input I/F 43 (after performing the operation in step S5 after step S4 in FIG. 4), the control unit 44 may perform control to set the observation mode of the endoscope system 1 to the normal observation mode (so as to perform the operation in step S1 in FIG. 4).

According to the present embodiment, as the processing to detect the movement of the distal end portion 2*c* in at least one of step S3 and step S6 in FIG. 4, the movement detection unit 44*b* may perform, for example, processing to calculate an absolute value (|OCTA−CTB|) of a difference between a contrast value CTA calculated based on the line profile acquired from a predetermined reference image SGI and a contrast value CTB calculated based on a line profile acquired from the movement detection image MDI recorded in the image recording unit 44*a* as a feature value FVC indicating the movement of the distal end portion 2*c*. In such a case, for example, when the control unit 44 determines that the feature value FVC is equal to or higher than the threshold THC for at least one movement detection image MDI recorded in the image recording unit 44*a*, the control unit 44 can perform the operation in step S1. In the aforementioned case, for example, when the control unit 44 determines that the feature value FVC is less than the threshold THC for all the movement detection images MDI recorded in the image recording unit 44*a*, the control unit 44 can perform the operation in step S5 or step S8. Note that as the predetermined reference image SGI, for example, an image including a structure or a dent such as the middle nasal concha existing inside the nasal cavity in the vicinity of the central part may be used.

The control unit 44 performs determination processing on whether an instruction for setting the observation mode of the endoscope system 1 to the normal observation mode has been executed (step S8 in FIG. 5).

When the control unit 44 has not successfully detected an instruction for setting the observation mode of the endoscope system 1 to the normal observation mode (S8: NO), the control unit 44 performs operation in step S9 in FIG. 5, which will be described later.

When the control unit 44 has successfully detected an instruction for setting the observation mode of the endoscope system 1 to the normal observation mode (S8: YES), the control unit 44 performs the operation in step S1 in FIG. 4. In other words, when the operation in step S1 is performed after step S8, the observation mode of the endoscope system 1 is switched from the diagnosis support mode to the normal observation mode in accordance with the operation of the observation mode switchover switch in the diagnosis support mode, and the display image displayed on the display apparatus 5 is switched from the diagnosis support image SDS to the endoscopic image WDI.

The control unit 44 performs determination processing on whether a release instruction has been executed or not (step S9 in FIG. 5).

When the control unit 44 has not successfully detected a release instruction (S9: NO), the control unit 44 performs the operation in step S5 in FIG. 4. In other words, when the operation in step S5 is performed after step S8 and step S9, the observation mode of the endoscope system 1 is maintained in the diagnosis support mode, and as the display image displayed on the display apparatus 5, the diagnosis support image SDS is maintained.

When the control unit 44 has successfully detected a release instruction (S9: YES), the control unit 44 causes the image recording unit 44a to record the endoscopic image SDI outputted through the image processing unit 41 as the release image SDR (step S10 in FIG. 5) and then performs operation in step S5 in FIG. 4. In other words, when the operation in step S5 is performed after step S8 to step S10, the observation mode of the endoscope system 1 is maintained in the diagnosis support mode, and as the display image displayed on the display apparatus 5, the diagnosis support image SDS is maintained.

According to the present embodiment, when the control unit 44 has successfully detected a release instruction in step S9 in FIG. 5, the control unit 44 may perform operation to record the endoscopic image SDI outputted through the image processing unit 41 in the image recording unit 44a as the release image SDR and then perform control to set the observation mode of the endoscope system 1 to the normal observation mode (perform the operation in step S1 in FIG. 4). According to such an operation, the observation mode of the endoscope system 1 is switched from the diagnosis support mode to the normal observation mode in accordance with the operation of the release switch in the diagnosis support mode, and the display image displayed on the display apparatus 5 is switched from the diagnosis support image SDS to the endoscopic image WDI.

As described so far, according to the present embodiment, immediately before the observation mode of the endoscope system 1 is switched from the normal observation mode to the diagnosis support mode, if the feature value indicating the movement of the distal end portion 2c is determined to be equal to or higher than a predetermined threshold, the operation to shift the observation mode of the endoscope system 1 to the diagnosis support mode is interrupted. According to the present embodiment, immediately before the observation mode of the endoscope system 1 is switched from the normal observation mode to the diagnosis support mode, if it is determined that the feature value indicating the movement of the distal end portion 2c is not equal to or higher than a predetermined threshold, the operation to shift the observation mode of the endoscope system 1 to the diagnosis support mode is performed. As described so far, according to the present embodiment, in the diagnosis support mode, if it is determined that the feature value indicating the movement of the distal end portion 2c is equal to or higher than the predetermined threshold, operation to shift the observation mode of the endoscope system 1 to the normal observation mode or operation to notify a state related to the movement of the distal end portion 2c of the endoscope 2 is performed. Therefore, according to the present embodiment, it is possible to secure safety when performing observation with images obtained by processing at least one of a color and a pattern of the endoscopic image.

Note that by modifying the configuration according to the present embodiment as appropriate, control to emit the same illumination light WL as illumination light in the normal observation mode from the light source apparatus 3 may be performed in the diagnosis support mode and control to display the diagnosis support image WDS obtained by processing at least one of a color and a pattern of the endoscopic image WDI obtained by image pickup of the object irradiated with the illumination light WL on the display apparatus 5 may be performed. In such a case, the diagnosis support image WDS may be generated using, for example, a method similar to the method for the diagnosis support image SDS.

Note that although a case has been mainly described above where the present invention is an endoscope system, the present invention is not limited to this, but the present invention may also be an operation method for operating the endoscope system as described above or a computer program for causing a computer to execute processing similar to the processing of the endoscope system or a non-transitory computer-readable storage medium configured to store (or record, the same shall apply hereinafter) the computer program.

Here, several examples of the storage medium storing a computer program product include a movable storage medium such as a flexible disk or CD-ROM or storage medium such as a hard disk. What is stored in a storage medium is not only a whole of the computer program but also part of the computer program. The whole or part of the computer program may be circulated or provided via a communication network. The user may install the computer program from the storage medium to the computer or download the computer program via a communication network and install the computer program in the computer so that the computer reads the computer program, executes the whole or part of operation, and can thereby perform operation of the aforementioned endoscope system.

The present invention is not limited to the aforementioned embodiment, but it goes without saying that various changes or applications can be made without departing from the spirit and scope of the invention.

What is claimed is:

1. An endoscope system comprising:
a processor configured to:
control a light source to switch between generating first illumination light and second illumination light;
receive an instruction to switch from a first observation mode in which a first image is obtained by an image pickup sensor based on illumination with the first illumination light to a second observation mode in which a third image is obtained by processing at least one of a color and a pattern of a second image obtained by the image pickup sensor based on illumination with the second illumination light;
calculate a first feature value indicating a first amount of movement of a distal end portion of an endoscope provided with the image pickup sensor based on the first image;
determine whether the first amount of movement of the distal end portion of the endoscope, indicated by the first feature value, before switching from the first observation mode to the second observation mode, is equal to or higher than a first predetermined threshold; and
in response to determining that the first amount of movement before switching from the first observation mode to the second observation mode is equal to or higher than the first predetermined threshold, maintain the first observation mode.

2. The endoscope system according to claim 1, wherein the processor is configured to:
in response to determining that the first amount of movement before switching from the first observation mode to the second observation mode is not equal to or higher than the first predetermined threshold, switch from the first observation mode to the second observation mode.

3. The endoscope system according to claim 1, wherein the processor is configured to:
calculate a second feature value indicating a second amount of movement of the distal end portion of the endoscope provided with the image pickup sensor based on the second image;
determine whether the second amount of movement of the distal end portion of the endoscope, indicated by the second feature value, in the second observation mode, is equal to or higher than a second predetermined threshold; and
in response to determining that the second amount of movement, indicated by the second feature value, in the second observation mode, is equal to or higher than the second predetermined threshold, switch from the second observation mode to the first observation mode.

4. The endoscope system according to claim 3, wherein the processor is configured to:
acquire a plurality of the second image obtained by the image pickup sensor based on illumination with the second illumination light, the plurality of second image comprising a first movement detection image and a second movement detection image; and
calculate the second feature value indicating the second amount of movement of the distal end portion of the endoscope based on pixel values of pixels included in the first movement detection image and pixel values of pixels included in the second movement detection image.

5. The endoscope system according to claim 4, wherein the second movement detection image is acquired a predetermined time period after the first movement detection image is acquired, and
wherein the second feature value is calculated based on the pixel values included in the first movement detection image and the second movement detection image and the predetermined time period.

6. The endoscope system according to claim 1, wherein the processor is configured to:
calculate a second feature value indicating a second amount of movement of the distal end portion of the endoscope provided with the image pickup sensor based on the second image;
determine whether the second amount of movement of the distal end portion of the endoscope, indicated by the second feature value, in the second observation mode, is equal to or higher than the second predetermined threshold; and
in response to determining that the second amount of movement, indicated by the second feature value, in the second observation mode, is equal to or higher than the second predetermined threshold, control to display visual information that can notify a state related to the movement of the distal end portion of the endoscope along with the third image.

7. The endoscope system according to claim 1, wherein the processor is configured to:
detect that a predetermined time period elapsed after switching to the second observation mode; and
in response to detecting that the predetermined time period elapsed, switch from the second observation mode to the first observation mode.

8. The endoscope system according to claim 1, wherein the processor is configured to:
in response to determining that the first amount of movement before switching from the first observation mode to the second observation mode is not equal to or higher than the first predetermined threshold, switch from the first observation mode to the second observation mode;
receive a release instruction for recording the second image as a still image; and
in response to receiving the release instruction in the second observation mode, record the second image as the still image and then switch from the second observation mode to the first observation mode.

9. The endoscope system according to claim 1, wherein the processor is configured to calculate the first feature value based on a pixel value of each pixel included in a predetermined calculation region set in accordance with a distance from a center of a movement detection image corresponding to the first image.

10. The endoscope system according to claim 1, wherein the processor is configured to calculate the first feature value based on a pixel value of each pixel included in a predetermined calculation region set in accordance with a distance from an end portion of a movement detection image corresponding to the first image.

11. The endoscope system according to claim 1, wherein the processor is configured to calculate the first feature value based on a contrast value calculated based on a line profile acquired from a predetermined reference image and a contrast value calculated based on a line profile acquired from a movement detection image corresponding to the first image.

12. The endoscope system according to claim 1, wherein the processor is configured to:
sequentially record the first image for each of a first predetermined time period before the instruction for switching from the first observation mode to the second observation mode is executed and a second predetermined time period corresponding to a time period continuous to the first predetermined time period after the instruction for switching from the first observation mode to the second observation mode is executed; and
calculate the first feature value indicating the first amount of movement of the distal end portion of the endo scope based on the first image sequentially recorded.

13. The endoscope system according to claim 1, wherein the processor is configured to:
acquire a plurality of the first image obtained by the image pickup sensor based on illumination with the first illumination light, the plurality of first image comprising a first movement detection image and a second movement detection image; and
calculate the first feature value indicating the first amount of movement of the distal end portion of the endoscope based on pixel values of pixels included in the first movement detection image and pixel values of pixels included in the second movement detection image.

14. The endoscope system according to claim 13, wherein the second movement detection image is acquired a predetermined time period after the first movement detection image is acquired, and
wherein the first feature value is calculated based on the pixel values included in the first movement detection image and the second movement detection image and the predetermined time period.

15. The endoscope system according to claim 1, wherein the second illumination light includes light having a center wavelength between 415 nm and 495 nm, inclusive of 415 nm and 495 nm.

16. The endoscope system according to claim 1, further comprising:
the light source; and
the image pickup sensor.

17. A method for operating an endoscope system, the method comprising:
switching between generating first illumination light and second illumination light;
receiving an instruction to switch from a first observation mode in which a first image is obtained by an image pickup sensor based on illumination with the first illumination light to a second observation mode in which a third image is obtained by processing at least one of a color and a pattern of a second image obtained by the image pickup sensor based on illumination with the second illumination light;
calculating a first feature value indicating an amount of movement of a distal end portion of an endoscope provided with the image pickup sensor based on the first image;
determining whether the amount of movement of the distal end portion of the endoscope, indicated by the first feature value, before switching from the first observation mode to the second observation mode, is equal to or higher than a first predetermined threshold; and
in response to determining that the amount of movement before switching from the first observation mode to the second observation mode is equal to or higher than the first predetermined threshold, maintaining the first observation mode.

18. A non-transitory computer-readable storage medium that stores a computer program, the computer program causing a computer to at least perform:
switching between generating first illumination light and second illumination light;
receiving an instruction to switch from a first observation mode in which a first image is obtained by an image pickup sensor based on illumination with the first illumination light to a second observation mode in which a third image is obtained by processing at least one of a color and a pattern of a second image obtained by the image pickup sensor based on illumination with the second illumination light;
calculating a first feature value indicating an amount of movement of a distal end portion of an endoscope provided with the image pickup sensor based on the first image;
determining whether the amount of movement of the distal end portion of the endoscope, indicated by the first feature value, before switching from the first observation mode to the second observation mode, is equal to or higher than a first predetermined threshold; and
in response to determining that the amount of movement before switching from the first observation mode to the second observation mode is equal to or higher than the first predetermined threshold, maintaining the first observation mode.

* * * * *